(12) United States Patent
Yagi

(10) Patent No.: US 8,507,016 B2
(45) Date of Patent: Aug. 13, 2013

(54) ALOE POWDER, ALOE JUICE, AND METHOD FOR PRODUCING THE SAME

(76) Inventor: Shunichi Yagi, Shizuoka (JP)

(*) Notice: Subject to any disclaimer, the term of this patent is extended or adjusted under 35 U.S.C. 154(b) by 296 days.

(21) Appl. No.: 12/925,380

(22) Filed: Oct. 20, 2010

(65) Prior Publication Data

US 2011/0038906 A1 Feb. 17, 2011

Related U.S. Application Data

(62) Division of application No. 11/597,217, filed as application No. PCT/JP2004/007329 on May 21, 2004, now abandoned.

(51) Int. Cl.
*A61K 36/886* (2006.01)
(52) U.S. Cl.
USPC .......................................................... 424/744
(58) Field of Classification Search
USPC .......................................................... 424/744
See application file for complete search history.

(56) References Cited

FOREIGN PATENT DOCUMENTS

| JP | 11-192054 | * | 7/1999 |
| JP | 2000-042406 | * | 2/2000 |
| JP | 2002-068997 | * | 3/2002 |

OTHER PUBLICATIONS

Avila H, Rivero J, Herrera F, Fraile G. Cytotoxicity of a low molecular weight fraction from Aloe vera (*Aloe barbadensis* Miller) gel. Toxicon. Sep. 1997;35(9):1423-30.*
Nahar Ms, Zhang J, Nakamura S. Influence of Biogeochemical Qualitites of Shizuoka Water on the Degradation of PVC Shower Hose. Journal of Environmental Protection. 2011:2; 204-212.*
Wang X, White-Hull C, Dyer S, Mitsova-Boneva D, Ghode M. United States Drinking Water Quality Study Report. 2007.*

* cited by examiner

*Primary Examiner* — Paul Zarek
(74) *Attorney, Agent, or Firm* — Hedman & Costigan, P.C.; James V. Costigan; Kathleen A. Costigan

(57) ABSTRACT

In the conventional technology, macromolecular polysaccharides, which the aloe vera gel inherently has, are broken down into small molecules for the following reasons: First, cellulose is broken down by the enzyme such as cellulose; Second, agitation in the cellulose breakdown process by the enzyme of cellulase and the like is performed in a heated state for an extended period of time; Third, nearly the same technique is employed also in the aloin absorption process by the activated charcoal; Fourth, a plurality of times of filtering causes intense oxidation to the gel juice. For the reasons described above, the molecular weight of macromolecular polysaccharides, which the aloe vera gel inherently has, is reduced to 80,000 dalton or less. Therefore, by use of the conventional technology, it is impossible to provide macromolecular polysaccharides that the aloe vera gel has in a state where aloin is removed.
To solve the above-mentioned problem, we provide aloe powder which is made from aloe vera gel, characterized by that a molecular weight of polysaccharides contained in the powder is not less than 400,000 dalton and an aloin content ratio of the powder is not more than 50 ppm.

3 Claims, 5 Drawing Sheets

ALOE POWDER, ALOE JUICE, AND METHOD FOR PRODUCING THE SAME

This application is a division of Ser. No. 11/597,217, filed Nov. 21, 2006 which claims priority to PCT/JP2004/007329, filed May 21, 2004.

TECHNICAL FIELD TO WHICH THE INVENTION BELONGS

The present invention is to provide powder and juice made from aloe vera gel while maintaining the molecular weight of macromolecular polysaccharides such as mannose and glucose as high as that in a raw material and in a state where aloin which is problematic if contained in large quantities is removed. The present invention is to provide clean and natural macromolecular powder and macromolecular juice for the health care industry, pharmaceutical industry, food industry and cosmetics industry.

RELATED ART

In a conventional technology, the following method has been typically adopted as a technique for removing aloin. First, gel of aloe vera is squeezed, crushed and agitated to obtain juice. Next, cellulose in which aloin exists is broken down by use of enzymes such as cellulase and cellulose is removed by filtering. Subsequently, activated charcoal or the like is thrown in to absorb aloin diffused in the juice in the foregoing cellulose breakdown process. Thereafter, filtering is performed again to remove the activated charcoal which has absorbed aloin. Accordingly, the juice is dried by use of SD or FD and crushed to obtain powder or remains the juice as it is. Alternatively, juice is obtained after concentration. Therefore, only powder and juice, which contains only polysaccharides whose molecular weight is lower than those contained in a raw material, have been heretofore provided because of the aloin removal process described above.

Problems to be Solved by the Invention

In the conventional technology, macromolecular polysaccharides, which the aloe vera gel inherently has, are broken down into small molecules for the following reasons: First, cellulose is broken down by the enzyme such as cellulase; Second, agitation in the cellulose breakdown process by the enzyme of cellulase and the like is performed in a heated state for an extended period of time; Third, nearly the same technique is employed also in the aloin absorption process by the activated charcoal; Fourth, a plurality of times of filtering causes intense oxidation to the gel juice. For the reasons described above, the molecular weight of macromolecular polysaccharides, which the aloe vera gel inherently has, is reduced to 80,000 dalton or less. Therefore, by use of the conventional technology, it is impossible to provide macromolecular polysaccharides that the aloe vera gel has in a state where aloin is removed.

The relationship between human beings and aloe vera up to around 1960 is basically the relationship between human beings and a raw material of aloe vera gel. For more than 2000 years, various efficacy of aloe vera on humans has been highly regarded as folk medicine. In other words, it can be easily imagined that macromolecular polysaccharides which aloe vera specifically has must have been the main reason of the efficacy.

However, up to the present date, provision of macromolecular polysaccharides such as mannose and glucose in a state where aloin is removed had never been realized.

The present invention is to provide, in the form of powder or juice, macromolecular polysaccharides which aloe vera inherently has even in a state where aloin is removed. The present invention is also intended to demonstrate, for human health, effects of aloe vera on diabetes and on human cells through provision of materials for clinical health care and the like.

Meanwhile, the method for removing aloin according to the conventional technology is extremely complicated and also far from being industrially predominant in terms of its accuracy.

Moreover, in the case of attempting to dry gel of a moisture content percentage of about 99.5% in a state where aloin is removed while maintaining the molecular weight of macromolecular polysaccharides by use of an aloin removal method of the present invention, it is difficult to remove moisture up to a low moisture content percentage by means of freeze dry or spray dry. This might be because of strong bond between moisture in macromolecular polysaccharides and polysaccharides. Thus, it is impossible to reduce the moisture content percentage of the dried body down to a level of 5% or less with almost no occurrence of component destruction. Therefore, if aloin is removed by use of the conventional method, drying up to the low moisture content percentage is possible since the macromolecular polysaccharide is broken down into small molecules. However, as in the case of the present invention of removing aloin while maintaining the molecular weight of macromolecular polysaccharides, it is basically impossible to dry up to the low moisture content percentage of 5% or less. Therefore, it is impossible to produce powder that has good preservation quality and a small particle size.

Moreover, in producing concentrated juice, an enzyme is deactivated by heating in the middle of or after a concentration process. Accordingly, sterilization is performed by means of ultraviolet irradiation or the like. The processes described above are all harsh on the gel. Thus, the gel is severely oxidized.

The method for removing aloin and the drying method according to the present invention enable provision of macromolecular polysaccharides, which had been heretofore sacrificed, for the first time in the state where aloin is removed.

Moreover, recently, regulations on aloin tend to become stricter in Europe than in the United States. Specifically, the regulations are to be made on a residual volume of aloin to 0.1 ppm or less. By use of a method for producing aloe powder according to any one of Claims 5 to 7, it is made possible to sufficiently respond to the regulations.

Meanwhile, as to the aloe juice, it is confirmed by the present invention that numerical values which fulfill the regulations in Europe described above have been already derived.

Consequently, it is made possible to perceive the aloe vera gel, which is a very compatible component with human cells, in terms of industrial production and to provide excellent physical properties of the macromolecular polysaccharides for a great number of consumers.

Means for Solving the Problems

Immersion of the aloe vera gel in water or a very dilute solution leads to an action of equilibrating the concentration by liquid, which occurs when a plurality of kinds of soluble liquid are mixed together. This is because a phenomenon close to the action of equilibrating the concentration, which occurs when different kinds of liquid are mixed with each other, appears since the moisture content percentage of the aloe vera gel is as extremely high as about 99.5%. Meanwhile, aloin exists in cellulose existing on a surface of the gel or inside thereof. This aloin is also a water-soluble fluid and cannot be prevented from the action of equilibrating the concentration. Because of its high concentration, aloin is rather subjected to the most drastic concentration equilibration.

Specifically, water enters into cellulose in which aloin exists and dilutes aloin with the passage of time. Accordingly, the diluted aloin moves toward water in a tank due to the action of equilibrating the concentration. Thereafter, this action is carried out until the concentration of continuously diluted aloin approaches as closely as possible to an ion concentration of the water in the tank. Specifically, most of the aloin existing in the gel is removed.

Meanwhile, macromolecular polysaccharides such as mannose and glucose, which are essential components, have a very high molecular weight. In addition, the macromolecular polysaccharides are unlikely to move because of their molecular bond and are unlikely to flow out toward water or a dilute solution. According to analyses, it is found out that the molecular weight of these macromolecular polysaccharides is 10,000,000 dalton or more. Consequently, it is found out that, because of their extremely high molecular weight, the macromolecular polysaccharides are unlikely to flow out.

Therefore, due to the action of equilibrating the concentration by liquid, aloin eventually flows out toward the water or the extremely dilute solution while being diluted. Meanwhile, most of the macromolecular polysaccharides remain inside the gel.

In using the very dilute solution, basically, effects closely analogous to those in a state where the gel is immersed in the water can be expected by setting the ion concentration of the solution to be lower than that in a state where the gel is turned into juice.

Consequently, from the aloe vera gel which has aloin removed thereof and sufficiently contains the macromolecular polysaccharides such as mannose, powder and juice which contain almost no aloin and have intrinsic macromolecular performance of a raw material are produced.

Moreover, in the case where purified water is used as the water in which the gel is immersed for the aloin removal, components such as chlorine, which is contained in the gel in relatively large quantities, sodium, magnesium and calcium can be reduced. Thus, the case proves high applicability to materials of medical ingredients, health care, pharmaceutical, food, drink, cosmetics and the like.

The reason why the molecular weight of polysaccharides is set to 400,000 dalton in the present invention is as follows:

According to analyses, even though the molecular weight of macromolecular polysaccharides by use of the production method of the present invention is 3,000,000 dalton or more, it has to be said that the molecular weight is lowered in comparison with a raw gel. The human beings have been using aloe vera for over 2000 years. The macromolecular polysaccharides such as macromolecular mannose and macromolecular glucose, which are specific to aloe vera, are nothing other than what have supported the long history. This is because it was only 50 years ago that provision of the powder and juice for the human beings started by the scientific technology and the raw gel had been basically used before that. Therefore, it is required to provide macromolecular polysaccharides closely analogous to the macromolecular polysaccharides that the raw gel has.

According to the analyses, the molecular weight of the macromolecular polysaccharides by use of the production method of the present invention is as extremely high as 3,000,000 dalton or more. However, in comparison with the raw gel, it has to be said that the molecular weight is lowered. This lowering is also caused by the aloin removal process as suspected. However, when aloin is removed by use of the conventional technology, the molecular weight is lowered to 80,000 dalton or less, which is the status quo.

Consequently, from the concept of polymers, the molecular weight of macromolecular polysaccharides which is considered to be impossible to achieve by use of the conventional technology is 400,000 dalton or more. It is desirable to provide powder and juice with the molecular weight of preferably 1,000,000 dalton or more, further preferably 3,000,000 dalton or more.

The reason why an aloin content ratio of the powder is set to 50 ppm or less and that of the juice is 10 ppm or less is as follows;

In consideration of the fact that the regulated value of aloin content ratio in the United States is 50 ppm or less, the aloin content ratio of the powder is set to 50 ppm or less. The production method of the present invention has already realized 10 ppm or less. This is also what is included in the range since 10 ppm is less than 50 ppm. Moreover, if the powder is finished to have a value close to 50 ppm or less, immersion time of the gel in the water can be shortened. Thus, high-volume productivity is improved.

Meanwhile, in Europe, it has been already said that regulations for reducing the aloin content ratio close to 0 ppm may be started. In response thereto, the present invention is also intended to enable provision of macromolecular polysaccharides as well.

In the case of the juice, based on the idea that the powder is diluted, since aloin content of the powder is 50 ppm or less, an aloin content ratio of the raw juice is 0.25 ppm, which is $\frac{1}{200}$ of that of the powder. However, as in the case of the powder, in the present invention, when aloin is removed by immersing the gel in the water, the immersion time can be shortened as long as an aloin residual volume is within the regulated range. Thus, in the case of the juice, the aloin content ratio is set to 10 ppm or less.

The reason why an average particle size of the aloe powder is set to 100 μm or less is as follows:

Numerical value of average particle size that is set to be fulfilled for the powder is determined on the grounds that the powder produced according to the present invention, that is, the powder sufficiently containing macromolecular polysaccharides of 400,000 dalton or more has good solubility and dispersibility in the water when the average particle size is 100 μm or less. Since the aloe powder according to the present invention has a small bulk specific gravity, it is difficult to finely crush the aloe powder. However, drying up to the low moisture content percentage according to the present application makes it possible to produce the powder having the average particle size of 100 μm or less. As the maximum level at the present stage, powder of the average particle size of 5 μm in the 1% range of water content has been successfully produced.

The reason why a chlorine content ratio of the powder is set to 2.5% or less and that of the juice is set to 250 ppm or less is as follows.

In production of cosmetics produced from aloe, chlorine is a substance which is wished to be eliminated as much as possible. In the aloin removal method of the present invention, if purified water is used as the water in which the gel is immersed, reduction of the chlorine content ratio to 0.7% for the powder and, therefore, reduction thereof to 35 ppm for the raw juice have been successful. However, from the viewpoint of productivity based on the immersion time in the water, the chlorine content ratio of the powder is set to 2.5% or less and that of the juice is set to 250 ppm or less, which is a value of double-concentrated juice.

Meanwhile, for production of the powder and the juice which are described above, a drying system is adopted, which uses microwave heating under reduced pressure or simultaneously performs the microwave heating and far infrared heating under reduced pressure. It is found out that, by use of the technology described above, drying or concentration can be performed while causing almost no damage in the gel and without lowering the molecular weight of the macromoleculars.

According to a drying experiment in accordance with the present invention, the moisture content percentage can be reduced to 2% in a state where almost no component destruction occurs. With this moisture content percentage, production of powder of the particle size of 5 μm or less is achieved. Accordingly, more highly efficient absorption into human body has been successful.

Meanwhile, in the case of concentration, during a concentration process in accordance with the present invention, short-time heating is performed in an environment with little oxygen and under a situation where moisture in the gel is reduced. Thus, oxidation hardly occurs and enzyme deactivation and sterilization can be surely carried out.

After heating with an upper limit of 90° C. is performed in the concentration process, various methods are conceivable such as continuing concentration by continuing to heat while reducing pressure, and performing concentration after lowering a temperature of the gel by stopping heating and reducing pressure. Thus, the present invention is not constrained by the process after high-temperature heating.

Moreover, in all aspects of the present invention, various drying methods and concentration methods are conceivable. Thus, as to items other than the drying method in the method for producing aloe powder and the concentration method in the method for producing aloe juice in accordance with the present invention, the present invention is not constrained by the drying method and the concentration method.

Moreover, as to the crushing method for powder production, various techniques are also conceivable, such as a jet mill technique and a freeze crushing technique. Thus, the present invention is not constrained by the crushing method.

Moreover, in the method for producing aloe powder, the aloin content ratio is successfully reduced to about 10 ppm. However, it could hardly be said that the method can sufficiently respond to the regulations which are being recently employed in Europe, in other words, the regulations for setting the aloin content ratio to 0.1 ppm or less. Thus, in order to further remove aloin slightly remaining after most of the aloin is removed, and processing is carried out as follows:

After aloin is removed, the gel is crushed and agitated, or is crushed and agitated after predetermined concentration, slightly remaining aloin is removed by removing cellulose through filtration, and then drying and crushing are performed.

After aloin is removed, the gel is crushed and agitated, or is crushed and agitated after predetermined concentration is performed, an activated charcoal is mixed in and agitated, slightly remaining aloin is absorbed in the activated charcoal, the activated charcoal, having aloin absorbed therein is removed by filtration, and then drying and crushing are performed.

After aloin is removed, the gel is crushed and agitated, or is crushed and agitated after predetermined concentration is performed, cellulose is removed by filtration, an activated charcoal is mixed in the gel having cellulose removed thereof and agitated, any remaining aloin is absorbed in the activated charcoal, the activated charcoal having aloin absorbed therein is removed by filtration, and then drying and crushing are performed.

In the method for producing powder and the method for producing juice, which are described above, catabolic enzyme such as cellulase is not used. Thus, molecular weight of the macromolecular polysaccharides which the gel inherently has are maintained.

As the water or the very dilute solution which is used for aloin removal, purified water is ideal in terms of the ion concentration. However, it is found out that aloin is sufficiently removed even if tap water which sanitation is secured is used. Since various kinds of water are conceivable depending on the ion concentration or the like, the present invention is not constrained by the ion concentration and the kind of the water or the extremely dilute solution.

Moreover, regarding a state of the water or the extremely dilute solution, in which the gel is immersed, various states are conceivable such as temperature setting, whether or not to use running water, whether or not to perform agitation and whether or not to use means for changing stored water. Thus, the present invention is not constrained by these items either.

Moreover, as to the kind of the extremely dilute solution, various kinds of solutions are conceivable, including, for example, a malic acid dilute solution, an amino acid dilute solution and the like. Thus, the present invention is not constrained by the kind of the dilute solution either.

Moreover, as to kinds of preservatives added for preserving the juice, various kinds are also conceivable. Thus, the present invention is not constrained by the kinds of preservatives added to the aloe juice or the amount of addition.

Moreover, according to analyses, when the method for performing the microwave heating under reduced pressure or simultaneously performing the microwave heating and the far infrared heating under reduced pressure is adopted as the drying system, the following result is obtained. Specifically, each of over ten times of experimental analyses, the general viable cell count is 300 CFU/g, which is close to 0, and no fungi or yeast is detected. Thus, the system also shows an effect of sterilization. However, even if other sterilization methods are adopted, the present invention is not constrained by the sterilization method or a sterilization process.

PREFERRED EMBODIMENTS OF THE INVENTION

Example 1

Figure 1:
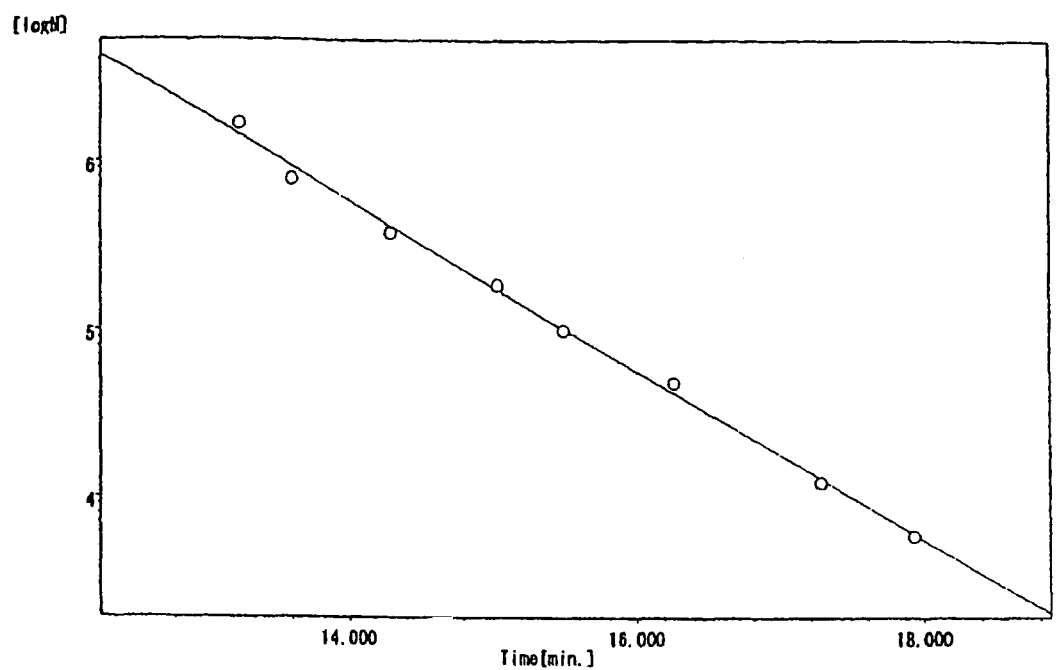
FIG. 1: Calibration curve for pullulan standards on a TSK-gel GMPW.

An analytical experiment is carried out for aloin removal and residual properties of macromolecular polysaccharides.

After epidermis of aloe vera is removed, gel is immersed as it is in drinkable tap water. A water tank has a form that makes agitation and overflow possible. Accordingly, immersion up to 24 hours is performed for each gel with different immersion period while continuously supplying a small amount of water. When the immersion period has passed, the gel is taken out of the water tank, heated simultaneously with microwaves and far infrared rays under reduced pressure and dried up to a moisture content percentage of about 2%. Next, the gel is crushed into powder. Subsequently, by use of high-performance liquid chromatography, residual aloin, mannose and glucose of the powder are analyzed according to respective immersion period. The following "0 hour immersion" in the list means a situation before immersion is performed and control values are listed in a column thereof.

|  | Aloin | Mannose | Glucose |
|---|---|---|---|
| 0 hour immersion | 760 ppm | 5.05% | 2.45% |
| 8 hour immersion | 106 ppm | 5.00% | 2.40% |
| 16 hour immersion | 25 ppm | 4.95% | 2.36% |
| 24 hour immersion | 17 ppm | 4.85% | 2.31% |

As described above, it is proven that aloin is removed in a state where component loss of macromolecular polysaccharides is extremely small. Considering that an aloin residual ratio of the powder in the case of 24 hour immersion is 17 ppm, an aloin residual ratio of juice is considered to be equivalent to that obtained by diluting the residual ratio of the powder by about 100 times for a double concentration and by about 200 times for a raw material. Thus, a level of 0.2 ppm or less for the double concentration and a value of 0.1 ppm or less for the raw material are already achieved.

Moreover, when aloin removal is carried out by use of a similar experimental method and a solution in which a very minute amount of malic acid is dissolved, an aloin removal rate is about the same as that by use of the tap water. In addition, more residues of malic acid, which is a component of aloe vera, are found out than the case of using the tap water. The residues of 13.5 g/100 g are found in the case of the tap water and the residues of 16.2 g/100 g are found in the case of the malic acid solution.

Example 2

An experimental analysis is carried out for removal of aloin and chlorine.

After epidermis of aloe vera is removed, the aloe vera is divided into 6 pieces and immersed in purified water. Thereafter, a state of running water is created as in the case of Example 1 and 24 hour immersion is performed by continuously supplying a small amount of purified water. Accordingly, the analysis is carried out in such a manner that the gel is taken out in 24 hours, subjected to microwave heating under reduced pressure to be dried up to a moisture content percentage of about 4% and crushed.

|  | Aloin | Chlorine |
|---|---|---|
| 0 hour immersion | 560 ppm | 4.2 g/100 g |
| 24 hour immersion | 10 ppm | 0.9 g/100 g |

As described above, it is confirmed that not only aloin but also a considerable amount of chlorine, which is wished to be eliminated in producing drugs and cosmetics, is removed.

Example 3

A molecular weight analysis of aloe powder is carried out.

In a raw aloe vera gel, about 74,000,000 dalton is marked at a peak start point, 16,000,000 dalton is marked at a peak top point and 260,000 dalton is marked at a peak end point.

The molecular weight is about 11,000,000 dalton.

Meanwhile, in a solution obtained by diluting the powder, which is produced by use of the method of the invention, by 200 times, about 71,000,000 dalton is marked at a peak start point, about 780,000 dalton is marked at a peak top point and about 20,000 dalton is marked at a peak end point.

The molecular weight is about 3,000,000 dalton.

On the other hand, when commercial freeze-dried powder is analyzed by use of a similar method, its molecular weight is only about 20,000 dalton.

A molecular weight analysis described above of the raw aloe vera gel and the powder produced by use of the method of the invention will be described below.

Note that the sample listed as Powder of Aloe Vera Gel processed by HYPER-DRY is the powder produced by use of the method of the invention. HYPER-DRY is a Japanese Registered Trademark owned by the applicant/inventor of this International application with the number, No. 4342207. HYPER-DRY is a drying apparatus which actualizes drying of far better quality than any similar previous apparatus, by adopting energy effect of microwave, far-infrared rays and reducing pressure simultaneously.

Figure 2:
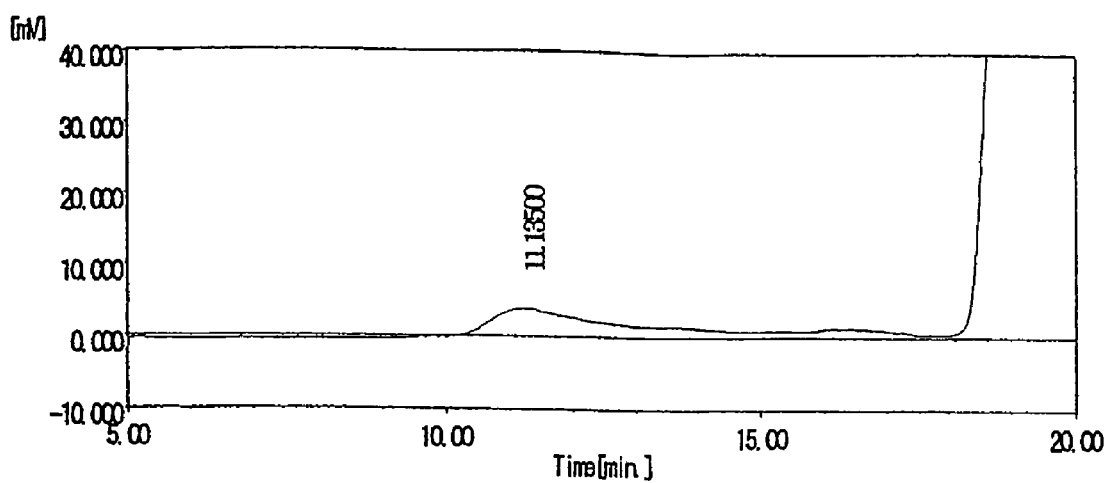
FIG. 2: Chromatogram of Aloe Vera Gel sample.
Figure 3:
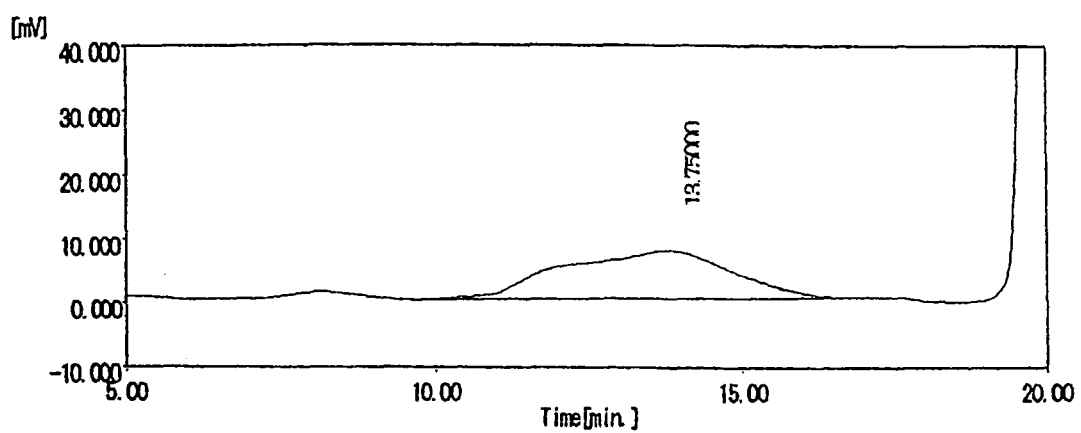
FIG. 3: Chromatogram of Powder of Aloe Vera Gel processed by HYPER-DRY sample.

Comparison of sample's Mw between Aloe Vera Gel and Powder of Aloe Vera Gel processed by HYPER-DRY is described in FIG. 1, FIG. 2 and FIG. 3.

FIG. 1 shows a calibration curve for pullulan standards on a TSKgel GMPW.

FIG. 1: Calibration curve for pullulan standards on a TSKgel GMPW. Column: TSKgel GMPW, two 10 μm, 7.8 mm×30 cm column in series. Sample: 100 μL of pullulan standards (1660000, 788000, 380000, 186000, 1000000, 48000, 12200 and 5800). Eluent: 0.2M NaNO$_3$. Flow rate 1.0 mL/min. Temperature: 40° C. Detection: Refractive Index detector (RI).

$$Mw = \Sigma nM^2 / \Sigma M \qquad \text{Appendix 1}$$

M is the molecular weight, n is the mole fraction, and Mw is the weight average molecular weight.

FIG. 2 shows a chromatogram of Aloe Vera Gel sample.

FIG. 2: Chromatogram of Aloe Vera Gel Sample.

Column: TSKgel GMPW, two 10 μm, 7.8 mm×30 cm column in series Eluent 0.2M NaNO$_3$. Flow rate 1.0 mL/min. Temperature: 40° C. Detection: RI. Sample treatment: 1 g of Aloe Vera Gel sample was homogenized in 2 mL of 0.2M NaNO$_3$ in a homogenizer. Then, centrifugation of homogenate at 2000×g, one minute was done. Upper solution was introduced as 200 μL aliquots Size Exclusion Chromatography (SEC).

FIG. 2 shows the elution profiles of Aloe Vera Gel sample processed by SEC. Peak start point is 9.85 minutes, where the molecular weight is 74,400,015. Peak top point is 11.14 minutes, where the molecular weight is 16,598,502. Peak end point is 14.69 minutes, where the molecular weight is 261,312. Mw is 11,480,389.

FIG. 3 shows a chromatogram of Powder of Aloe Vera Gel processed by HYPER-DRY sample.

FIG. 3 shows Chromatogram of Powder of Aloe Vera Gel processed by HYPER-DRY sample.

Column: TSKgel GMPW, tow 10 μm, 7.8 mm×30 cm columns in series. Eluent: 0.2M NaN03. Flow rate; 1.0 mL/min. Temperature: 40° C. Detection: RI. Sample treatment: 1 g of Powder of Aloe Vera Gel processed by HYPER-DRY sample was dissolved in 200 mL of 0.2M NaNO3. Then, centrifugation of sample solution at 2000×g, one minute was done. Upper solution was introduced as 200 μL aliquots to SEC.

FIG. 3 shows the elution profiles of Powder of Aloe Vera Gel processed by HYPER-DRY sample by SEC. Peak start point is 9.86 minutes, where the molecular weight is 71,421,303. Peak top point is 13.75 minutes, where the molecular weight is 783,872. Peak end point is 16.80 minutes, where the molecular weight is 22,408. Mw is 3,101,743. FIGS. 2 and 3 were analyzed in same conditions.

Example 4

Experimental production of aloe powder having an average particle size of 5 μm is carried out.

About 20 kg of gel from which aloin is removed by immersing the gel for 28 hours in purified water is set as it is in a vacuum tank. The gel is heated simultaneously with 5 kw of microwaves and 0.8 kw of far infrared rays under reduced pressure and dried up to a moisture content percentage of 1.5%. FIG. 1 is a chart of the drying. After the drying is finished, by use of a jet mill of about 18000 rpm, the gel is crushed into powder of the average particle size of 5.09 μm.

When physical properties of the minute powder are analyzed, the following result is obtained:
Residual aloin: 10 ppm, Contained mannose 4.92%,
Contained glucose: 2.45%, Contained malic acid: 15.0 g/100 g,
Contained lactic acid: 0.0 g/100 g, General viable cell count: $1.2 \times 10^1$/g
Residual chlorine: 0.7 g/100 g, Moisture content: 2.1%

Note that, when viscosity of a solution obtained by diluting 1 g of the minute powder in 200 cc of purified water is observed, sufficient viscosity is obtained. Thus, it is confirmed that a macromolecular property of polysaccharides is sufficiently maintained.

Moreover, it is also confirmed that, in comparison with powder of the particle size of 80 m, the powder of the particle size of 5 μm has a higher penetration rate into skin.

Example 5

As an example, an experiment is carried out for confirming further reduction of aloin. After epidermis of aloe vera is removed, the aloe vera is divided into 6 pieces and immersed in purified water tank in a state of running water for 24 hours. Next, concentration is performed to remove 50% of moisture contained in the gel and the gel is crushed and agitated. Thereafter, filtration of cellulose is performed. Subsequently, the filtered gel is set in a vacuum tank, heated simultaneously with microwaves and far infrared rays under reduced pressure to be dried up to a moisture content percentage of 3% and crushed. As a result of an analysis, it is confirmed that an aloin residual ratio is 1.2 ppm.

Moreover, when aloin removal is performed by use of a similar method and an activated charcoal, the aloin residual ratio is 2.5 ppm.

Furthermore, when aloin removal is further performed by use of the activated charcoal after cellulose is removed, the aloha residual ratio is 0.5 ppm.

From the results described above, it is found out that the aloin residual ratio can be reduced close to 0.

Example 6

Production of powder according to Claim 8 is carried out.

After epidermis of aloe vera is removed, the aloe vera is divided into 6 pieces and immersed in purified water for 28 hours. The purified water is in a running state where the water is agitated in a purified water tank. In addition, small amount of purified water is continuously supplied thereto and the flooded purified water flows out of the tank. Thus, the purified water in the tank is always maintained to be fresh.

The gel is taken out of the tank at a stage where the immersion is finished and mounted on a tray as it is. About 3 kg of gel is mounted on 1 tray and a total of about 36 kg of gel on 12 trays are set in a vacuum tank. A rotation jig is formed to have 4 stairs and 3 trays are mounted on each of the stairs.

In the example, 12 kw of microwave output and 1.6 kw of far infrared heater output are adopted.

Drying is performed under control as shown in the following chart.

Far infrared heating is subjected to PID control and used for rapid evaporation of moisture emerging on a surface of the gel. A constitution is adopted so that the surface always reaches 60° C. by use of a sensor. The sensor is turned on throughout the process.

The microwave output is set to 12 kw until about 90% of moisture of the gel is removed and is changed to 6 kw through a stopping stage. The microwave output can be further changed to 2 kw through a stopping stage.

A vacuum pump has output of 15 kw and is formed to enable pressure transition at around 4 kPa when the microwave output is 12 kw. A temperature applied to the gel when the microwave output is 12 kw is only about 29° C., which is about the same as a vapor pressure temperature of water under 4 kPa. This is because a cooling action occurs all the time in the gel itself due to heat taken away from the gel by evaporation. Moreover, since drying is performed in an environment with extremely little oxygen, oxidation hardly occurs. Thus, a very good dried body of gel can be obtained.

Figure 4:
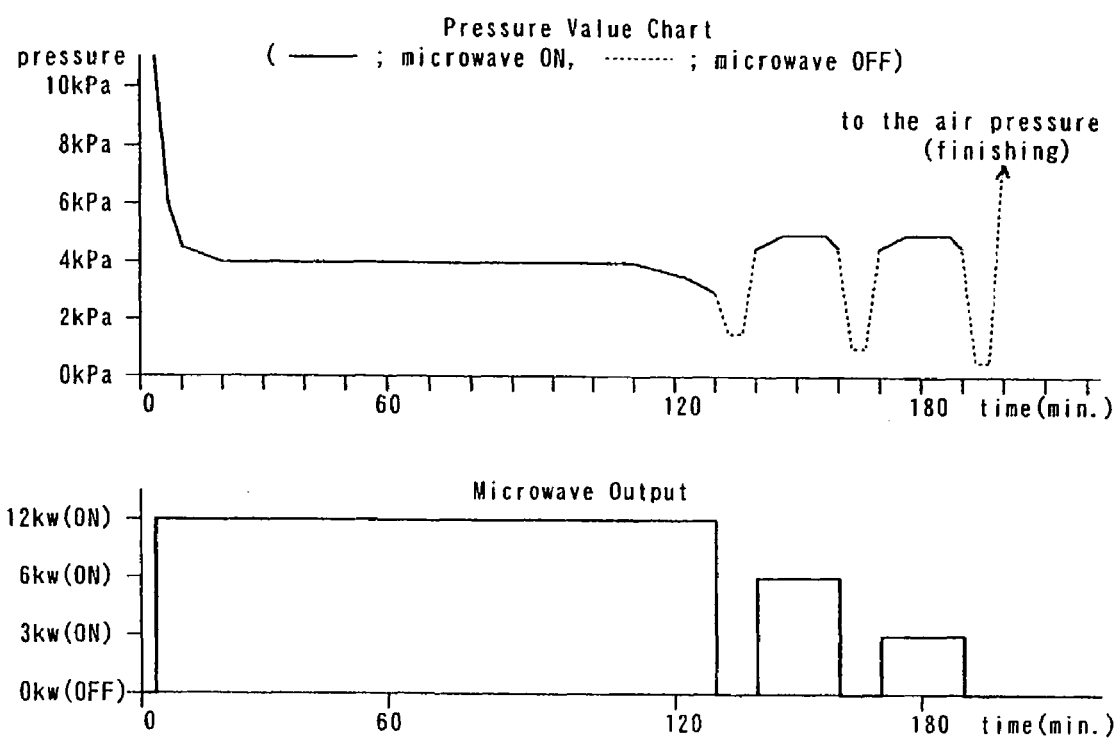
FIG. 4; Chart example of drying process according to the invention.

Transition of a drying process of the example is described in FIG. 4; DRYING PROCESS EXAMPLE.

As a result, a dried body of gel which shows no change in color and has a moisture content percentage of 3% is obtained. As a result of a molecular weight analysis, the molecular weight exceeds 3,000,000 dalton as in the case of Example 3. Moreover, the residual aloin ratio is 8 ppm. When the gel is crushed into powder by use of a jet mill, the average particle size thereof is about 40 μm.

Meanwhile, when the gel, which is subjected to similar aloin removal processing, is freeze-dried, the limit of drying is the moisture content percentage of 14%. Thus, it is difficult to produce powder.

Example 7

Production of concentrated juice according to Claim 15 is carried out.

After epidermis of aloe vera is removed, the aloe vera is divided into 3 pieces and immersed in a purified water tank for 24 hours by use of a method similar to that of Example 6. Next, 12 kg of gel having aloin removed thereof are mounted on trays. Specifically, 1 kg of gel is mounted on each of the trays and 3 trays are mounted on each of 4 stairs in a rotation jig. The rotation jig is set in a vacuum tank and a concentration process is started by use of microwave heating. 8 kw of microwave output is adopted. In the drying method, a moisture removal amount per 1 kw per 1 minute can be calculated as about 22.5 g. Thus, at a stage where 40 minutes have passed, in other words, about 50% of moisture contained in the gel before concentration is removed based on the calculated value, a vacuum valve is closed while continuing the microwave heating. Accordingly, heating is performed while maintaining a pressure in the tank at 75 kPa by opening a pressure recovery valve. Based on measurement by use of a fiber thermometer, a temperature of the gel is kept in a temperature zone of 85° C. to 90° C. for 2 minutes. In this case, since the pressure is managed, cooling of the gel occurs due to heat of evaporation under a vapor pressure of water. Thus, the inside and outside the gel is maintained at 85° C. to 90° C. Therefore, heating accuracy is extremely high. Next, pressure reduction is performed by stopping the microwave heating, closing the pressure recovery valve and opening the vacuum valve. When the pressure reduction is continued for 5 minutes to lower the temperature of the gel, the pressure in the tank reaches 1.6 kPa. Subsequently, pressure recovery is performed and the concentration is completed. The temperature of the gel when the gel is taken out of the vacuum tank is 15° C. Moreover, the amount of removed moisture is 53% of the initial moisture amount.

Figure 5:
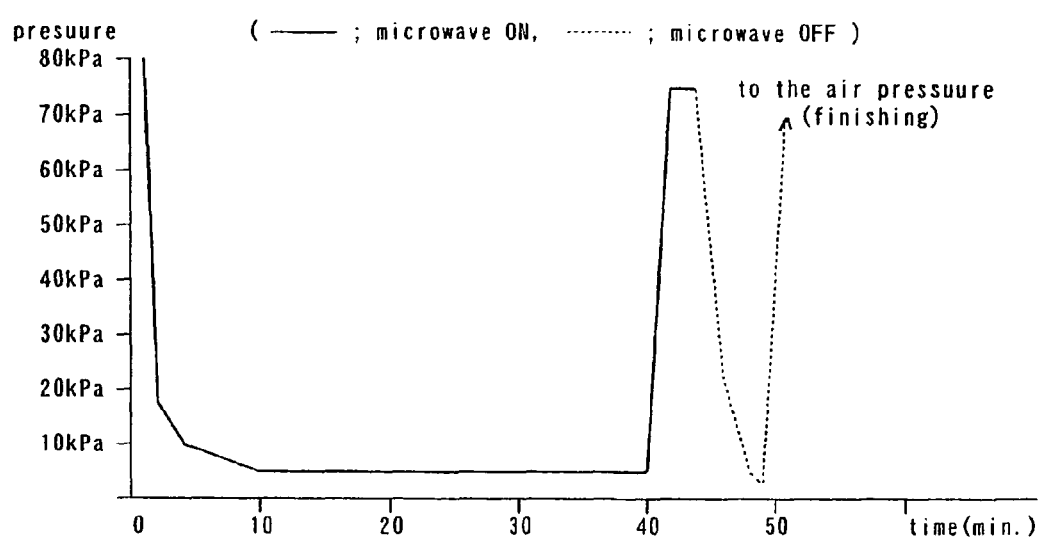
FIG. 5: Chart example of concentration process according to the invention.

Transition of a concentrating process of the example is described in FIG. 5; CONCENTRATING PROCESS EXAMPLE.

As a result of an analysis, a general viable cell count is $1 \times 10^1$/g.

Moreover, comparison with concentrated juice processed without performing heating is carried out by refrigerating the juice at 5° C. and comparing in terms of an organoleptic test on odor, a bacterial growth analysis and an item of residual viscosity properties of macromolecular polysaccharides.

The concentrated juice subjected to no heating emits odor on the $8^{th}$ day of preservation. However, the juice concerned in the experiment emits no odor even on the $20^{th}$ day of preservation. Moreover, in the juice subjected to no heating, $3 \times 10^4$ of bacteria are detected on the $7^{th}$ day of preservation and the viscosity of macromolecular polysaccharides is reduced by half. On the other hand, in the juice concerned in the experiment, only $2 \times 10^2$ of bacteria are detected on the $18^{th}$ day of preservation and the viscosity is hardly changed.

From the results described above, it is found out that the method for producing concentrated juice according to the invention brings about an exceptional result in terms of the preservation quality since enzyme deactivation and sterilization are already performed in the concentration process. Moreover, the enzyme deactivation and the sterilization are completed within the same process under reduced pressure. Thus, it is possible to obtain high-quality aloe juice which is hardly deteriorated by oxidation of the gel or the like.

EFFECTS OF THE INVENTION

The present invention can provide powder or juice of macromolecular polysaccharides which aloe vera inherently has in a state where aloin is removed. The present invention is also intended to demonstrate, for human health, effects of aloe vera on diabetes and on human cells through provision of materials for clinical health care and the like.

The method for removing aloin and the drying method according to the present invention enable, for the first time in the state where aloin is removed, provision of macromolecular polysaccharides, which had been heretofore sacrificed.

In the case of removing aloin while maintaining the molecular weight of the macromolecular polysaccharides as in the case of the present invention, drying up to the low moisture content percentage of 5% or less is possible. Therefore, it is possible to produce powder that has good preservation quality and a small particle size.

Moreover, conventionally, in producing a concentrated juice, an enzyme is deactivated by heating in the middle of or after a concentration process. Accordingly, sterilization is performed by means of ultraviolet irradiation or the like. The processes described above are harsh on the gel. Thus, the gel is severely oxidized. However, the method for removing aloin and the drying method according to the present invention enable, for the first time in the state where aloin is removed, the provision of macromolecular polysaccharides, which had been heretofore sacrificed.

Moreover, recently, regulations on aloin tend to become stricter in Europe than in the United States. However, by use of the method for producing aloe powder according to the invention, it is made possible to sufficiently respond to the regulations.

Meanwhile, as to the aloe juice, the present invention has already derived numerical values which fulfill the regulations in Europe described above.

Consequently, it is made possible to perceive the aloe vera gel, which) is a very compatible component with human cells, in terms of industrial production, and to, provide excellent physical properties of the macromolecular polysaccharides for a great number of consumers.

The invention claimed is:

1. A method for producing aloe powder, wherein a molecular weight of polysaccharides contained in the aloe powder is 3,000,000 dalton or more, and wherein an aloin content ratio of the aloe powder is not more than 25 ppm, characterized in that said method comprises the steps of:
    immersing a gel of aloe vera in water for a time period of 16-28 hours, wherein the gel of aloe vera is in either a state where only a skin of the aloe vera is removed, or in a state where the skin is removed and the gel of aloe vera is divided into pieces, without crushing and agitating the gel of aloe vera, thereby reducing the aloin content ratio of the gel of aloe vera to not more than 25 ppm;
    drying said gel of aloe vera under a reduced pressure of 4 kPa to obtain a dried gel of aloe vera; and
    crushing said dried gel of aloe vera to obtain aloe powder having a molecular weight of 3,000,000 dalton or more.

2. The method for producing the aloe powder according to claim 1, wherein the gel of aloe vera, after reducing the aloin content ratio to not more than 25 ppm, is dried to a moisture content of not more than 5% by placing the said aloe vera gel in a vacuum tank, performing either microwave heating or simultaneous heating with microwave and far infrared rays, under a reduced pressure of 4 kPa, and then crushing the dried gel of aloe vera into powder.

3. The method for producing the aloe powder according to claim 1, wherein the aloe powder obtained by drying and crushing the gel of aloe vera is formed to have an average particle size of not more than 100 μm.

* * * * *